(12) United States Patent
Dugger, III et al.

(10) Patent No.: US 8,236,285 B2
(45) Date of Patent: *Aug. 7, 2012

(54) BUCCAL, POLAR AND NON-POLAR SPRAY CONTAINING ZOLPIDEM

(75) Inventors: Harry A. Dugger, III, Flemington, NJ (US); Mohammed Abd El-Shafy, Hauppauge, NY (US)

(73) Assignee: Novadel Pharma Inc., Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,457

(22) Filed: Oct. 9, 2009

(65) Prior Publication Data

US 2010/0092403 A1    Apr. 15, 2010

Related U.S. Application Data

(60) Continuation of application No. 11/384,444, filed on Mar. 21, 2006, now abandoned, which is a division of application No. 10/671,715, filed on Sep. 29, 2003, now Pat. No. 7,632,517, which is a continuation-in-part of application No. 10/230,060, filed on Aug. 29, 2002, now abandoned, which is a continuation-in-part of application No. 09/537,118, filed on Mar. 29, 2000, now abandoned, which is a continuation-in-part of application No. PCT/US97/17899, filed on Oct. 1, 1997.

(51) Int. Cl.
*A61K 9/12* (2006.01)
*A61F 13/00* (2006.01)

(52) U.S. Cl. ................... 424/45; 424/434; 424/435

(58) Field of Classification Search .............. None
See application file for complete search history.

(56) References Cited

U.S. PATENT DOCUMENTS

| 3,155,574 A | 11/1964 | Silson et al. |
| 3,304,230 A | 2/1967 | Abramson et al. |
| 3,784,684 A | 1/1974 | Bossert et al. |

(Continued)

FOREIGN PATENT DOCUMENTS

CN    99112590    12/1999

(Continued)

OTHER PUBLICATIONS

Maarek et al., "The Safety and Efficacy of Zolpidem in Insomniac Patients: A Long-Term Open Study in General Practice," *J. Int. Med. Res.*, 1992, 2091), 162-170.

(Continued)

*Primary Examiner* — Carlos Azpuru
*Assistant Examiner* — Casey Hagopian
(74) *Attorney, Agent, or Firm* — Dickstein Shapiro LLP

(57) ABSTRACT

Buccal aerosol sprays or capsules using polar and non-polar solvents have now been developed which provide zolpidem for rapid absorption through the oral mucosa, resulting in fast onset of effect. The buccal polar compositions of the invention comprise formulation I: aqueous polar solvent, zolpidem, and optional flavoring agent; formulation II: aqueous polar solvent, zolpidem, optionally flavoring agent, and propellant; formulation III: non-polar solvent, zolpidem, and optional flavoring agent; formulation IV: non-polar solvent, zolpidem, optional flavoring agent, and propellant; formulation V: a mixture of a polar solvent and a non-polar solvent, zolpidem, and optional flavoring agent; formulation VI: a mixture of a polar solvent and a non-polar solvent, zolpidem, optional flavoring agent, and propellant.

10 Claims, 1 Drawing Sheet

U.S. PATENT DOCUMENTS

| | | |
|---|---|---|
| 4,232,002 A | 11/1980 | Nogrady |
| 4,495,168 A | 1/1985 | Schmolka |
| 4,689,233 A | 8/1987 | Dvorsky et al. |
| 4,704,406 A | 11/1987 | Stanislaus et al. |
| 4,755,389 A | 7/1988 | Jones et al. |
| 4,814,161 A | 3/1989 | Jinks et al. |
| 4,857,312 A | 8/1989 | Hegasy et al. |
| 4,863,720 A * | 9/1989 | Burghart et al. ............... 424/45 |
| 4,863,970 A | 9/1989 | Patel et al. |
| 4,919,919 A | 4/1990 | Aouda et al. |
| 4,935,243 A | 6/1990 | Borkan et al. |
| 5,011,678 A | 4/1991 | Wang et al. |
| 5,047,230 A | 9/1991 | Nagy et al. |
| 5,128,132 A | 7/1992 | Parnell |
| 5,135,753 A | 8/1992 | Baker et al. |
| 5,143,731 A | 9/1992 | Viegas et al. |
| 5,166,145 A | 11/1992 | Jao et al. |
| 5,186,925 A | 2/1993 | Cholcha |
| 5,240,932 A | 8/1993 | Morimoto et al. |
| 5,290,540 A | 3/1994 | Prince et al. |
| 5,364,616 A | 11/1994 | Singer et al. |
| 5,370,862 A | 12/1994 | Klokkers-Bethke et al. |
| 5,428,006 A | 6/1995 | Bechgaard |
| 5,456,677 A | 10/1995 | Spector |
| 5,457,100 A | 10/1995 | Daniel |
| 5,474,759 A | 12/1995 | Fassberg et al. |
| 5,502,076 A | 3/1996 | Dixit et al. |
| 5,519,059 A | 5/1996 | Sawaya |
| 5,593,684 A | 1/1997 | Baker et al. |
| 5,602,182 A | 2/1997 | Popli et al. |
| 5,605,674 A | 2/1997 | Purewal et al. |
| 5,607,915 A | 3/1997 | Patton |
| 5,635,161 A | 6/1997 | Adjei et al. |
| 5,645,856 A | 7/1997 | Lacy et al. |
| 5,719,197 A * | 2/1998 | Kanios et al. ............... 514/772.6 |
| 5,725,841 A | 3/1998 | Duan et al. |
| 5,766,573 A | 6/1998 | Purewal et al. |
| 5,795,909 A | 8/1998 | Shashoua et al. |
| 5,824,307 A | 10/1998 | Johnson |
| 5,869,082 A | 2/1999 | Dugger, III |
| 5,891,465 A | 4/1999 | Keller et al. |
| 5,906,811 A | 5/1999 | Hersch |
| 5,908,611 A | 6/1999 | Gottlieb et al. |
| 5,910,301 A | 6/1999 | Farr et al. |
| 5,932,410 A | 8/1999 | Whittaker et al. |
| 5,955,098 A | 9/1999 | Dugger, III |
| 5,981,591 A | 11/1999 | Deihl |
| 6,071,539 A | 6/2000 | Robinson et al. |
| 6,110,486 A | 8/2000 | Dugger, III |
| 6,143,329 A | 11/2000 | Kim |
| 6,212,227 B1 | 4/2001 | Ko et al. |
| 6,258,032 B1 | 7/2001 | Hammesfahr |
| 6,271,240 B1 | 8/2001 | Simon |
| 6,299,900 B1 | 10/2001 | Reed et al. |
| 6,375,975 B1 | 4/2002 | Modi |
| 6,458,842 B1 | 10/2002 | Dickinson et al. |
| 6,512,002 B2 | 1/2003 | Lee et al. |
| 6,676,931 B2 | 1/2004 | Dugger |
| 6,706,255 B2 | 3/2004 | Dickinson et al. |
| 6,816,452 B1 | 11/2004 | Mahata |
| 6,969,508 B2 * | 11/2005 | Dugger, III ............... 424/45 |
| 6,977,070 B2 | 12/2005 | Dugger, III |
| 6,998,110 B2 * | 2/2006 | Dugger, III ............... 424/45 |
| 7,202,233 B2 | 4/2007 | Penkler |
| 2002/0102218 A1 | 1/2002 | Cowan |
| 2002/0110524 A1 | 8/2002 | Cowan et al. |
| 2003/0039680 A1 | 2/2003 | Dugger |
| 2003/0077227 A1 | 4/2003 | Dugger |
| 2003/0077228 A1 | 4/2003 | Dugger |
| 2003/0077229 A1 | 4/2003 | Dugger |
| 2003/0082107 A1 | 5/2003 | Dugger |
| 2003/0095925 A1 | 5/2003 | Dugger |
| 2003/0095926 A1 | 5/2003 | Dugger |
| 2003/0095927 A1 | 5/2003 | Dugger |
| 2003/0185761 A1 | 10/2003 | Dugger |
| 2003/0190286 A1 | 10/2003 | Dugger |
| 2003/0191180 A1 | 10/2003 | Ross |
| 2003/0211047 A1 | 11/2003 | Dugger |
| 2004/0062716 A1 | 4/2004 | Dugger |
| 2004/0120895 A1 | 6/2004 | Dugger |
| 2004/0120896 A1 | 6/2004 | Dugger |
| 2004/0136913 A1 | 7/2004 | Adb El Shafy Mohammed et al. |
| 2004/0136914 A1 | 7/2004 | Dugger et al. |
| 2004/0136915 A1 | 7/2004 | Dugger et al. |
| 2004/0141923 A1 | 7/2004 | Dugger et al. |
| 2004/0265239 A1 | 12/2004 | Dugger et al. |
| 2005/0002867 A1 | 1/2005 | Dugger et al. |
| 2005/0025712 A1 | 2/2005 | Dugger |
| 2005/0025713 A1 | 2/2005 | Dugger |
| 2005/0025714 A1 | 2/2005 | Dugger |
| 2005/0025715 A1 | 2/2005 | Dugger |
| 2005/0025716 A1 | 2/2005 | Dugger |
| 2005/0025717 A1 | 2/2005 | Dugger |
| 2005/0142069 A1 | 6/2005 | Dugger, III |
| 2005/0163719 A1 | 7/2005 | Dugger et al. |
| 2005/0180923 A1 | 8/2005 | Dugger et al. |
| 2005/0281752 A1 | 12/2005 | Dugger, III |
| 2005/0281753 A1 | 12/2005 | Dugger, III |
| 2005/0287075 A1 | 12/2005 | Dugger, III |
| 2006/0159624 A1 | 7/2006 | Dugger, III |
| 2006/0165604 A1 | 7/2006 | Dugger et al. |
| 2006/0171896 A1 | 8/2006 | Dugger et al. |
| 2006/0198790 A1 | 9/2006 | Dugger et al. |
| 2006/0210484 A1 | 9/2006 | Dugger et al. |
| 2006/0216240 A1 | 9/2006 | Dugger et al. |
| 2006/0216241 A1 | 9/2006 | Dugger et al. |
| 2006/0222597 A1 | 10/2006 | Dugger et al. |
| 2007/0048229 A1 | 3/2007 | Dugger et al. |

FOREIGN PATENT DOCUMENTS

| | | |
|---|---|---|
| DE | 3338978 | 5/1984 |
| DE | 3246081 | 6/1984 |
| DE | 4007705 | 9/1991 |
| DE | 4038203 | 6/1992 |
| DE | 4112303 | 10/1992 |
| DE | 4132176 | 4/1993 |
| EP | 0140434 | 5/1985 |
| EP | 0213108 | 3/1987 |
| EP | 0315960 | 5/1989 |
| EP | 0386700 | 9/1990 |
| EP | 0471161 | 2/1992 |
| EP | 0504112 | 9/1992 |
| EP | 0605483 | 4/1993 |
| EP | 0557129 | 8/1993 |
| EP | 0656206 | 6/1995 |
| EP | 0719549 | 7/1996 |
| EP | 1029536 | 8/2000 |
| EP | 2 042 161 A1 | 4/2009 |
| FR | 2633933 | 1/1990 |
| GB | 1154317 | 6/1969 |
| GB | 2082457 | 3/1982 |
| GB | 2291593 | 1/1996 |
| GB | 2295318 | 5/1996 |
| IE | 912509 A1 | 2/1992 |
| JP | 0226661 | 1/1990 |
| WO | WO 90/01046 | 2/1990 |
| WO | WO 92/04012 A | 3/1992 |
| WO | WO 93/03751 | 3/1993 |
| WO | WO 93/04671 | 3/1993 |
| WO | WO 9304671 A1 * | 3/1993 |
| WO | WO 94/07514 | 4/1994 |
| WO | WO 94/10987 | 5/1994 |
| WO | WO 94/13280 | 6/1994 |
| WO | WO 95/24893 | 9/1995 |
| WO | WO 95/31217 | 11/1995 |
| WO | WO 97/33621 | 9/1997 |
| WO | WO 97/38662 | 10/1997 |
| WO | WO 9738663 | 10/1997 |
| WO | WO 9738687 | 10/1997 |
| WO | WO 97/42938 A1 | 11/1997 |
| WO | WO 98/29097 | 7/1998 |
| WO | WO 98/34595 A1 | 8/1998 |
| WO | WO 98/52540 | 11/1998 |
| WO | WO 98/52545 | 11/1998 |
| WO | WO 99/16417 | 4/1999 |
| WO | WO 99/29097 | 6/1999 |
| WO | WO 00/06534 | 2/2000 |

| WO | WO 00/27359 | 5/2000 |
| WO | WO 00/62757 | 10/2000 |
| WO | WO 01/59142 | 8/2001 |
| WO | WO 01/60420 | 8/2001 |
| WO | WO 01/66089 | 9/2001 |
| WO | WO 01/72338 | 10/2001 |
| WO | WO 02/43695 | 6/2002 |
| WO | WO 02/066089 | 8/2002 |
| WO | WO 02/094232 | 11/2002 |
| WO | WO 02/094234 | 11/2002 |
| WO | WO 2006/089082 A2 | 8/2006 |

OTHER PUBLICATIONS

Schlich, D., et al., "Long-term treatment of insomnia with zolpidem: a multicentre general practitioner study of 107 patients." *The Journal of International Medical Research*, 1991, 19(3), pp. 271-279.

Cosdon, Christina K., "Sprays sold as better way to get vitamins," *Seminole Times; Seminole Business Digest*, Nov. 6, 1996.

Cassidy et al., "Controlled Buccal Delivery of Buprenorphine," *Journal of Controlled Release*, 25 (1993) 21-29.

Shojaei, A. H. "Buccai Mucosa As a Route for Systemic Drug Delivery: a Review," J. Pharm. Pharmaceut. Sci. 1998, 1(1), pp. 15-30.

*Goodman and Gilman's The Pharmacological Basis of Therapeutics*, 9th ed., pp. 490.

*Goodman and Gilman's The Pharmacological Basis of Therapeutics*, 9th ed., pp. 496.

*Goodman and Gilman's The Pharmacological Basis of Therapeutics*, 9th ed., pp. 497.

*Goodman and Gilman's The Pharmacological Basis of Therapeutics*, 9th ed., pp. 471-472.

Rote Liste 1995 "Arzneimitteluerzeichnis des BPI and UFA".

Flemington Pharmaceutical Corporation webpage, www.flemington-pharma.com.

*Goodman and Gilman's The Pharmacological Basis of Therapeutics*, 9th ed., pp. 141-154, 169-170, 260, 303-304, 324, 362, 372, 420-422, 427, 471-472, 478-480, 484, 490, 496-497, 928-930.

Ye Jiang-Hong et al.; "Ondansetron Exhibits the Properties of a Local Anesthetic"; Anesthesia and Analgesia, vol. 85. No. 5, Nov. 1997; pp. 1116-1121.

Zervakis, et al.; "Taste Effects of Lingual Application of Cardiovascular Medications"; Physiology & Behavior, 68: pp. 405-413 (2000).

Mochizuki, et al.; Inhaled Diuretics Attenuate Acid-Induced Cough in Children With Asthma; Chest, 107/2 pp. 413-417 (1995).

Karlsson, et al.; "A Comparison of he Effect of Inhaled Diuretics on Airway Reflexes in Humans and Guinea Pigs", The American Physiological Society, pp. 434-438 (1992).

L.W. Brox, et al.; "Studies on the Growth Inhibition and Metabolism of 2'-Deoxy-2' fluorocytidine in Cultured Human Lymphoblasts"; Cancer Research vol. 34, pp. 1838-1842 (1974).

Ting-Chao Chou, et al.; "Pharmacological Disposition and Metabolic Fate of 2'-Fluoro-5-iodo-1-β-D-arabinofuranosylcytosine in Mice and Rats"; Caner Research vol. 41, pp. 3336-3342 (1981).

Woodley et al., Manual of Medical Therapeutics, 27th Edition, 1992, pp. 341 and 370-371.

Physician's Desk Reference, 1995, pp. 858-861, 2436-2441, 2548-2550.

Written Opinion of the International Searching Authority—Feb. 28, 2006.

Drug Facts and Comparisons (Jan. 2002) pp. 186c-186d.

Schlich, D, et al. "Long-term treatment of insomnia with zolpidem: a multicentre general practitioner study of 107 patients,"The Journal of International Medical Research, 1991, 19(3), pp. 271-279.

Maarek et al. "The Safety and Efficacy of Zolpidem in Insomniac Patients: a Long-Term Open Study in General Practice," J. Int. Med. Res. 1992, 20(2), 162-170.

* cited by examiner

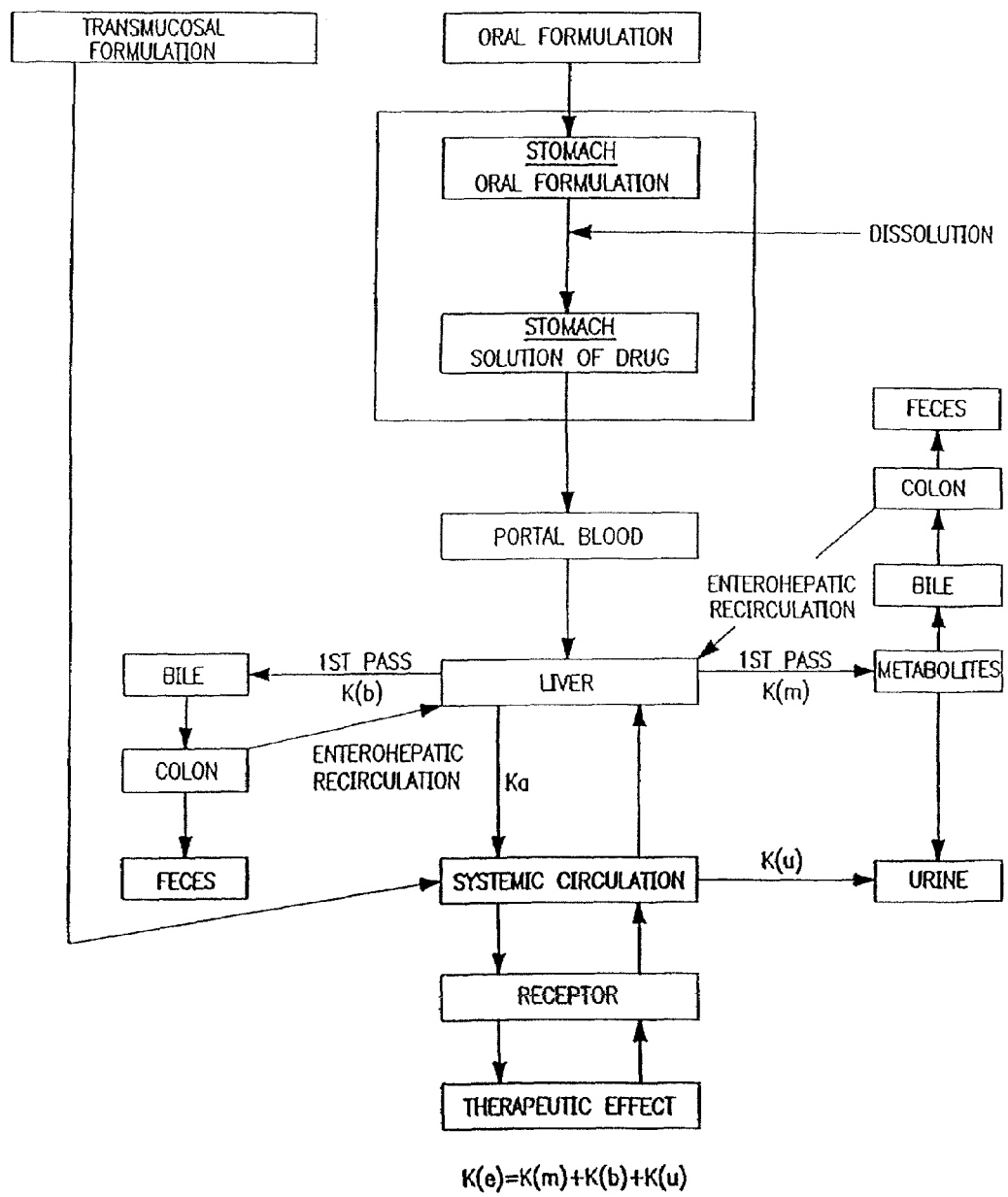

BUCCAL, POLAR AND NON-POLAR SPRAY CONTAINING ZOLPIDEM

CROSS REFERENCE TO RELATED APPLICATIONS

This application is a continuation application of application Ser. No. 11/384,444, filed Mar. 21, 2006, now abandoned which is a divisional of application Ser. No. 10/671,715, filed Sep. 29, 2003, now U.S. Pat. No. 7,632,517 which is a continuation-in-part of application Ser. No. 10/230,060, filed Aug. 29, 2002, now abandoned which is a continuation-in-part of application Ser. No. 09/537,118, filed Mar. 29, 2000 now abandoned which is a continuation-in-part of the U.S. national phase designation of PCT/US97/17899 filed Oct. 1, 1997, the disclosures of which are incorporated by reference herein in their entirety.

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered.

Zolpidem is a imidazopyridine having the structure shown below:

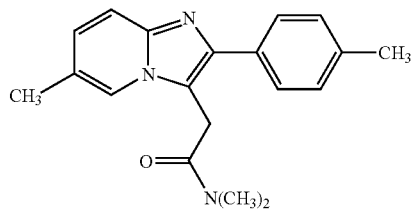

The chemical name for zolpidem is N,N, 6-trimethyl-2-p-tolyl-imidaz-o[1,2-a]pyridine-3-acetamide Zolpidem is a non-benzodiazepine sedative-hypnotic and is used to treat insomnia. To treat insomnia, zolpidem is typically administered orally at a dose of between 10 and 25 mg. Typically zolpidem is administered as the tartrate salt, i.e., N,N, 6-trimethyl-2-p-tolyl-imida-zo[1,2-a]pyridine-3-acetamide L-(+)-tartrate (2:1). Following discontinuation of zolpidem the beneficial effects on sleep can last for up to a week. Tolerance and physical dependence is only rarely observed with zolpidem. (Goodman and Gilman's *The Pharmacological Basis of Therapeutics*, 9$^{th}$ ed., pp. 471-472).

SUMMARY OF THE INVENTION

A buccal aerosol spray or soft bite gelatin capsule using a polar or non-polar solvent has now been developed which provides biologically active compounds for rapid absorption through the oral mucosa, resulting in fast onset of effect.

The buccal aerosol spray compositions of the present invention, for transmucosal administration of a pharmacologically active compound soluble in a pharmacologically acceptable non-polar solvent comprise in weight % of total composition: pharmaceutically acceptable propellant 5-80%, nonpolar solvent 19-85%, active compound 0.05-50%, suitably additionally comprising, by weight of total composition a flavoring agent 0.01-10%. Preferably the composition comprises: propellant 10-70%, non-polar solvent 25-89.9%, active compound 0.01-40%, flavoring agent 1-8%; most suitably propellant 20-70%, non-polar solvent 25-74.75%, active compound 0.25-35%, flavoring agent 2-7.5%.

The buccal polar aerosol spray compositions of the present invention, for transmucosal administration of a pharmacologically active compound soluble in a pharmacologically acceptable polar solvent are also administrable in aerosol form driven by a propellant. In this case, the composition comprises in weight % of total composition: aqueous polar solvent 10-97%, active compound 0.1-25%, suitably additionally comprising, by weight of total composition a flavoring agent 0.05-10% and propellant: 2-10%. Preferably the composition comprises: polar solvent 20-97%, active compound 0.1-15%, flavoring agent 0.1-5% and propellant 2-5%; most suitably polar solvent 25-97%, active compound 0.2-25%, flavoring agent 0.1-2.5% and propellant 2-4%.

In another embodiment, the buccal polar aerosol spray compositions of the present invention for transmucosal administration of a pharmacologically active compound (i.e., those administrable in aerosol form driven by a propellant) comprises a mixture of a polar solvent and a non-polar solvent comprising in weight % of total composition: solvent 10-97%, active compound 0.05-50%, propellant 5-80%, and optionally a taste mask and/or flavoring agent 0.01-10%. Preferably the composition comprises: solvent 20-97%, active compound 0.1-40%, propellant 10-70%, and taste mask and/or flavoring agent 1-8%; most suitably solvent 25-97%, active compound 0.25-35%, propellant 20-70%, and taste mask and/or flavoring agent 2-7.5%. The ratio of the polar solvent to the non-polar solvent can range from about 1:99 to about 99:1, preferable from about 60:40 to about 40:60, and more preferably about 50:50.

The buccal pump spray composition of the present invention, i.e., the propellant free composition, for transmucosal administration of a pharmacologically active compound wherein said active compound is soluble in a pharmacologically acceptable non-polar solvent comprises in weight % of total composition: non-polar solvent 30-99.69%, active compound 0.005-55%, and suitably additionally, flavoring agent 0.1-10%.

The buccal polar pump spray compositions of the present invention, i.e., the propellant free composition, for transmucosal administration of a pharmacologically active compound soluble in a pharmacologically acceptable polar solvent comprises in weight % of total composition: aqueous polar solvent 30-99.69%, active compound 0.001-60%, suitably additionally comprising, by weight of total composition a flavoring agent 0.1-10%. Preferably the composition comprises: polar solvent 37-98.58%, active compound 0.005-55%, flavoring agent 0.5-8%; most suitably polar solvent 60.9-97.06%, active compound 0.01-40%, flavoring agent 0.75-7.5%.

In another embodiment, the buccal pump spray composition (i.e., the propellant free composition) for transmucosal administration of a pharmacologically active compound comprises a mixture of a polar solvent and a non-polar solvent comprising in weight % of total composition solvent 30-99.69%, active compound 0.001-60%, and optionally a taste mask and/or flavoring agent 0.1-10%. Preferably the composition comprises: solvent 37-98.58%, active compound 0.005-55%, taste mask and/or flavoring agent 0.5-8%; more preferably the composition comprises solvent 60.9-97.06%, active compound 0.01-40%, and taste mask and/or flavoring agent 0.75-7.5%. The ratio of the polar solvent to the non-polar solvent can range from about 1:99 to about 99:1, preferable about 60:40 to about 40:60, and more preferably about 50:50.

The soft bite gelatin capsules of the present invention for transmucosal administration of a pharmacologically active compound, at least partially soluble in a pharmacologically acceptable non-polar solvent, having charged thereto a fill composition comprise in weight % of total composition: non-polar solvent 4-99.99%, emulsifier 0-20%, active compound 0.01-80%, provided that said fill composition contains less than 10% of water, suitably additionally comprising, by weight of the composition: flavoring agent 0.01-10%. Preferably, the soft bite gelatin capsule comprises: non-polar solvent 21.5-99.975%, emulsifier 0-15%, active compound 0.025-70%, flavoring agent 1-8%; most suitably: nonpolar solvent 28.5-97.9%, emulsifier 0-10%, active compound 0.1-65.0%, flavoring agent 2-6%.

The soft bite polar gelatin capsules of the present invention for transmucosal administration of a pharmacologically active compound, at least partially soluble in a pharmacologically acceptable polar solvent, having charged thereto a composition comprising in weight % of total composition: polar solvent 25-99.89%, emulsifier 0-20%, active compound 0.01-65%, provided that said composition contains less than 10% of water, suitably additionally comprising, by weight of the composition: flavoring agent 01-10%. Preferably, the soft bite gelatin capsule comprises: polar solvent 37-99.95%, emulsifier 0-15%, active compound 0.025-55%, flavoring agent 1-8%; most suitably: polar solvent 44-96.925%, emulsifier 0-10%, active compound 0.075-50%, flavoring agent 2-6%.

It is an object of the invention to coat the mucosal membranes either with fine droplets of spray containing the active compounds or a solution or paste thereof from bite capsules.

It is also an object of the invention to administer to the oral mucosa of a mammalian in need of same, preferably man, by spray or bite capsule, a predetermined amount of a biologically active compound by this method or from a soft gelatin capsule.

A further object is a sealed aerosol spray container containing a composition of the non polar or polar aerosol spray formulation, and a metered valve suitable for releasing from said container a predetermined amount of said composition.

As the propellant evaporates after activation of the aerosol valve, a mist of fine droplets is formed which contains solvent and active compound.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The non-polar solvent is a non-polar hydrocarbon, preferably a $C_{7-18}$ hydrocarbon of a linear or branched configuration, fatty acid esters, and triglycerides such as miglyol. The solvent must dissolve the active compound and be miscible with the propellant, i.e., solvent and propellant must form a single phase at a temperature of 0-40° C. a pressure range of between 1-3 atm.

The polar and non-polar aerosol spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, which does not allow entry of atmospheric gasses with each activation. Such containers are commercially available.

A further object is a pump spray container containing a composition of the pump spray formulation, and a metered valve suitable for releasing from said container a predetermined amount of said composition.

A further object is a soft gelatin bite capsule containing a composition of as set forth above. The formulation may be in the form of a viscous solution or paste containing the active compounds. Although solutions are preferred, paste fills may also be used where the active compound is not soluble or only partially soluble in the solvent of choice. Where water is used to form part of the paste composition, it should not exceed 10% thereof. (All percentages herein are by weight unless otherwise indicated.)

The polar or non-polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., for its teaching of such capsules. The capsules of the present invention are intended to be bitten into to release the low viscosity solution or paste therein, which will then coat the buccal mucosa with the active compounds. Typical capsules, which are swallowed whole or bitten and then swallowed, deliver the active compounds to the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatin: 50-75%, glycerin 20-30%, colorants 0.5-1.5%, water 5-10%, and sorbitol 2-10%.

The active compound may include, biologically active peptides, central nervous system active amines, sulfonyl ureas, antibiotics, antifungals, antivirals, sleep inducers, antiasthmatics, bronchial dilators, antiemetics, histamine H-2 receptor antagonists, barbiturates, prostaglandins and neutraceuticals.

The active compounds may also include antihistamines, alkaloids, hormones, benzodiazepines and narcotic analgesics. While not limited thereto, these active compounds are particularly suitable for non-polar pump spray formulation and application.

The active compounds may also include p-FOX (fatty acid oxidation) inhibitors, acetylcholinesterase inhibitors, nerve impulse inhibitors, anti-cholinergics, anti-convulsants, anti-psychotics, anxiolytic agents, dopamine metabolism inhibitors, agents to treat post stroke sequelae, neuroprotectants, agents to treat Alzheimer's disease, neurotransmitters, neurotransmitter agonists, sedatives, agents for treating attention deficit disorder, agents for treating narcolepsy, central adregenic antagonists, anti-depression agents, agents for treating Parkinson's disease, benzodiazepine antagonists, stimulants, neurotransmitter antagonists, tranquilizers, or a mixture thereof.

In one embodiment, the active compound is zolpidem or a pharmaceutically acceptable salt thereof.

BRIEF DESCRIPTION OF THE DRAWING

FIG. 1. is a schematic diagram showing routes of absorption and processing of pharmacologically active substances in a mammalian system.

DESCRIPTION OF THE PREFERRED EMBODIMENTS

The preferred active compounds of the present invention are in an ionized, salt form or as the free base of the pharmaceutically acceptable salts thereof (provided, for the aerosol or pump spray compositions, they are soluble in the spray solvent). These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40-99.99%) first pass effect.

As propellants for the non polar sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1-0.2%. All percentages herein are by weight unless otherwise indicated. It is also preferable that the propellant be synthetically produced to minimize the presence of contaminants which are harmful to the active compounds. These contaminants include oxidizing agents, reducing agents, Lewis acids or bases, and water. The concentration of each of these should be less than 0.1%, except that water may be as high as 0.2%.

Suitable non-polar solvents for the capsules and the non-polar sprays include ($C_2$-$C_{24}$) fatty acid ($C_2$-$C_{.6}$) esters, $C_7$-$C_{18}$ hydrocarbon, $C_2$-$C_6$ alkanoyl esters, and the triglycerides of the corresponding acids. When the capsule fill is a paste, other liquid components may be used instead of the above low molecular weight solvents. These include soya oil, corn oil, other vegetable oils.

As solvents for the polar capsules or sprays there may be used low molecular weight polyethyleneglycols (PEG) of 400-1000 Mw (preferably 400-600), low molecular weight ($C_2$-$C_8$) mono and polyols and alcohols of $C_7$-$C_{18}$ linear or branch chain hydrocarbons, glycerin may also be present and water may also be used in the sprays, but only in limited amount in the capsules.

It is expected that some glycerin and water used to make the gelatin shell will migrate from the shell to the fill during the curing of the shell. Likewise, there may be some migration of components from the fill to the shell during curing and even throughout the shelf-life of the capsule.

Therefore, the values given herein are for the compositions as prepared, it being within the scope of the invention that minor variations will occur.

The preferred flavoring agents are synthetic or natural oil of peppermint, oil of spearmint, citrus oil, fruit flavors, sweeteners (sugars, aspartame, saccharin, etc.), and combinations thereof.

The compositions may further include a taste mask. The term "taste mask" as used herein means an agent that can hide or minimize an undesirable flavor such as a bitter or sour flavor. A representative taste mask is a combination of vanillin, ethyl vanillin, maltol, iso-amyl acetate, ethyl oxyhydrate, anisic aldehyde, and propylene glycol (commercially available as "PFC 9885 Bitter Mask" from Pharmaceutical Flavor Clinic of Camden, N.J.). A taste mask in combination with a flavoring agent is particularly advantageous when the active compound is an alkaloid since alkaloids often have a bitter taste.

The active substances include the active compounds selected from the group consisting of cyclosporine, sermorelin, octreotide acetate, calcitonin-salmon, insulin lispro, sumatriptan succinate, clozepine, cyclobenzaprine, dexfenfluramine hydrochloride, glyburide, zidovudine, erythromycin, ciprofloxacin, ondansetron hydrochloride, dimenhydrinate, cimetidine hydrochloride, famotidine, phenyloin sodium, phenyloin, carboprost thromethamine, carboprost, diphenhydramine hydrochloride, isoproterenol hydrochloride, terbutaline sulfate, terbutaline, theophylline, albuterol sulfate and neutraceuticals, that is to say nutrients with pharmacological action such as but not limited to carnitine, valerian, echinacea, and the like.

In another embodiment, the active compound is a p-FOX (fatty acid oxidation) inhibitor, acetylcholinesterase inhibitor, nerve impulse inhibitor, anti-cholinergic, anti-convulsant, anti-psychotic, anxiolytic agent, dopamine metabolism inhibitor, agent to treat post stroke sequelae, neuroprotectant, agent to treat Alzheimer's disease, neurotransmitter, neurotransmitter agonist, sedative, agent for treating attention deficit disorder, agent for treating narcolepsy, central adregenic antagonist, anti-depression agent, agent for treating Parkinson's disease, benzodiazepine antagonist, stimulant, neurotransmitter antagonist, tranquilizer, or a mixture thereof.

In one embodiment the active compound is a p-FOX inhibitor. A suitable p-FOX inhibitor for use in the buccal sprays of the invention includes, but is not limited to, ranolazine.

In one embodiment the active compound is an acetylcholinesterase inhibitor. Suitable acetylcholinesterase inhibitors for use in the buccal sprays of the invention include, but are not limited to, galantamine, neostigmine, physostigmine, and edrophonium.

In one embodiment the active compound is a nerve impulse inhibitor. Suitable nerve impulse inhibitors for use in the buccal sprays of the invention include, but are not limited to, levobupivacaine, lidocaine, prilocalne, mepivacaine, propofol, rapacuronium bromide, ropivacaine, tubocurarine, atracurium, doxaurium, mivacurium, pancuronium, vercuronium, pipecuronium, and rocuronium.

In one embodiment the active compound is an anti-cholinergic. Suitable anti-cholinergics for use in the buccal sprays of the invention include, but are not limited to, amantadine, ipratropium, oxitropium, and dicycloverine.

In one embodiment the active compound is an anti-convulsant. Suitable anti-convulsants for use in the buccal sprays of the invention include, but are not limited to, acetazolamide, carbamazepine, clonazepam, diazepam, divalproex (valproic acid), ethosuximide, lamotrignine acid, levetriacetam, oxcarbazepine, phenobarbital, phenyloin, pregabalin, primidone, remacemide, trimethadione, topiramate, vigabatrin, and zonisamide.

In one embodiment the active compound is an anti-psychotic. Suitable anti-psychotics for use in the buccal sprays of the invention include, but are not limited to, amisulpride, aripiprazole bifemelane, bromperidol, clozapine, chlorpromazine, haloperidol, iloperidone loperidone, olanzapine, quetiapine, fluphenazine, fumarate, risperidone, thiothixene, thioridazine, sulpride, and ziprasidone, In one embodiment the active compound is an anxiolytic agent. Suitable anxiolytic agents for use in the buccal sprays of the invention include, but are not limited to, amitryptiline, atracurium, buspirone, chlorzoxazone, clorazepate, cisatracurium, cyclobenzaprine, eperisone, esopiclone, hydroxyzine, mirtazapine, mivacurium, pagoclone, sulperide, zaleplon, and zopiclone.

In one embodiment the active compound is a dopamine metabolism inhibitor. Suitable dopamine metabolism inhibitors for use in the buccal sprays of the invention include, but are not limited to, entacapone, lazebemide, selegiline, and tolcapone.

In one embodiment the active compound is an agent to treat post stroke sequelae. Suitable agents to treat post stroke sequelae for use in the buccal sprays of the invention include, but are not limited to, glatiramer, interferon beta 1A, interferon beta 1B, estradiol, and progesterone.

In one embodiment the active compound is a neuroprotectant. Suitable neuroprotectants for use in the buccal sprays of the invention include, but are not limited to, donepezil, memanine, nimodipine, riluzole, rivastigmine, tacrine, TAK147, and xaliproden.

In one embodiment the active compound is an agent to treat Alzheimer's disease. Suitable agents to treat Alzheimer's disease for use in the buccal sprays of the invention include, but are not limited to, carbidopa, levodopa, tacrine, donezepil, rivastigmine, and galantamine.

In one embodiment the active compound is a neurotransmitter. Suitable neurotransmitters for use in the buccal sprays of the invention include, but are not limited to, acetylcholine, serotonin, 5-hydroxytryptamine (5-HT), GABA, glutamate, aspartate, glycine, histamine, epinephrine, norepinephrine, dopamine, adenosine, ATP, and nitric oxide.

In one embodiment the active compound is a neurotransmitter agonist. Suitable neurotransmitter agonists for use in the buccal sprays of the invention include, but are not limited to, almotriptan, aniracetam, atomoxetine, benserazide, bromocriptine, bupropion, cabergoline, citalopram, clomipramine, desipramine, diazepam, dihydroergotamine, doxepin duloxetine, eletriptan, escitalopram, fluvoxamine, gabapentin, imipramine, moclobemide, naratriptan, nefazodone, nefiracetam acamprosate, nicergoline, nortryptiline, paroxetine, pergolide, pramipexole, rizatriptan, ropinirole, sertraline, sibutramine, sumatriptan, tiagabine, trazodone, venlafaxine, and zolmitriptan.

In one embodiment the active compound is a sedative. Suitable sedatives for use in the buccal sprays of the invention include, but are not limited to, dexmedetomidine, eszopiclone, indiplon, zolpidem, and zaleplon.

In one embodiment the active compound is an agent for treating attention deficit disorder. Suitable agents for treating attention deficit disorder for use in the buccal sprays of the invention include, but are not limited to, amphetamine, dextroamphetamine, methylphenidate, and pemoline.

In one embodiment the active compound is an agent for treating narcolepsy. Suitable agents for treating narcolepsy for use in the buccal sprays of the invention include, but are not limited to, modafinil and mazindol.

In one embodiment the active compound is a central adregenic antagonists. A suitable central adregenic antagonists for use in the buccal sprays of the invention includes, but is not limited to, mesoridazine.

In one embodiment the active compound is an anti-depression agent. Suitable anti-depression agents for use in the buccal sprays of the invention include, but are not limited to, amitriptyline, amoxapine, bupropion, clomipramine, clomipramine, clorgyline, desipramine, doxepin, fluoxetine, imipramine, isocarboxazid, maprotiline, mirtazapine, nefazodone, nortriptyline, paroxetine, phenelzine, protriptyline, sertraline, tranylcypromine, trazodone, and venlafaxine.

In one embodiment the active compound is an agent for treating Parkinson's disease. Suitable agents for treating Parkinson's disease for use in the buccal sprays of the invention include, but are not limited to, amantadine, bromocriptine, carvidopa, levodopa, pergolide, and selegiline.

In one embodiment the active compound is a benzodiazepine antagonist. A suitable benzodiazepine antagonist for use in the buccal sprays of the invention includes, but is not limited to, flumazenil.

In one embodiment the active compound is a neurotransmitter antagonist. A suitable neurotransmitter antagonist for use in the buccal sprays of the invention includes, but is not limited, to deramciclane.

In one embodiment the active compound is a stimulant. Suitable stimulants for use in the buccal sprays of the invention include, but are not limited to, amphetamine, dextroamphetamine, dinoprostone, methylphenidate, methylphenidate, modafinil, and pemoline.

In one embodiment the active compound is a tranquilizer. A suitable tranquilizer for use in the buccal sprays of the invention includes, but is not limited to, mesoridazine.

In a another embodiment, the active compound is zolpidem or a pharmaceutically acceptable salt thereof. In one embodiment, the active compound is zolpidem tartrate.

Typically, when zolpidem or a pharmaceutically acceptable salt thereof is the active compound the buccal spray contains from about 0.01 to 20 weight/weight (w/w) percent zolpidem, more preferably 0.1 to 15 w/w percent zolpidem, and most preferably 0.2 to 10 w/w percent zolpidem.

The invention further relates to a method of treating insomnia in a patient by spraying the oral mucosa of the patient with a therapeutically effective amount of a buccal spray comprising zolpidem or a pharmaceutically acceptable salt thereof.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal or man in need of same are to be determined by the treating physician.

The invention is further defined by reference to the following examples, which are intended to be illustrative and not limiting.

The following are examples of certain classes. All values unless otherwise specified are in weight percent.

EXAMPLES

Example 1

Biologically Active Peptides Including Peptide Hormones

|  | Amounts | preferred amount | most preferred amount |
|---|---|---|---|
| A. Cyclosporine lingual spray ||||
| cyclosporine | 5-50 | 10-35 | 15-25 |
| water | 5-20 | 7.5-50 | 9.5-12 |
| ethanol | 5-60 | 7.5-50 | 10-20 |
| polyethylene glycol | 20-60 | 30-45 | 35-40 |
| flavors | 0.1-5 | 1-4 | 2-3 |
| B. Cyclosporine Non-Polar lingual spray ||||
| cyclosporine | 1-50 | 3-40 | 5-30 |
| MIGLYOL ® | 20 | 25 | 30-40 |
| Polyoxyethylated castor oil | 20 | 25 | 30-40 |
| Butane | 25-80 | 30-70 | 33-50 |
| flavors | 0.1-5 | 1-4 | 2-3 |
| C. Cyclosporine non-polar bite capsule ||||
| cyclosporine | 1-35 | 5-25 | 10-20 |
| olive oil | 25-60 | 35-55 | 30-45 |
| polyoxyethylated oleic glycerides | 25-60 | 35-55 | 30-45 |
| flavors | 0.1-5 | 1-4 | 2-3 |
| D. Cyclosporine bite capsule ||||
| cyclosporine | 5-50 | 10-35 | 15-25 |
| polyethylene glycol | 20-60 | 30-45 | 35-40 |
| glycerin | 5-30 | 7.5-25 | 10-20 |
| propylene glycol | 5-30 | 7.5-25 | 10-20 |
| flavors | 0.1-10 | 1-8 | 3-6 |
| E. Sermorelin (as the acetate) lingual spray ||||
| sermorelin (as the acetate) | .01-5 | .1-3 | .2-1.0 |
| mannitol | 1-25 | 5-20 | 10-15 |
| monobasic sodium phosphate, | 0.1-5 | 1-31 | .5-2.5 |
| dibasic sodium phosphate | 0.01-5 | .05-3 | 0.1-0.5 |
| water ||||
| ethanol | 5-30 | 7.5-25 | 9.5-15 |
| polyethylene glycol | 20-60 | 30-45 | 35-40 |
| propylene glycol | 5-25 | 10-20 | 12-17 |
| flavors | 0.1-5 | 1-4 | 2-3 |
| F. Octreotide acetate (Sandostatin) lingual spray ||||
| octreotide acetate | 0.001-0.5 | 0.005-0.250 | 0.01-0.10 |
| acetic acid | 1-10 | 2-8 | 4-6 |
| sodium acetate | 1-10 | 2-8 | 4-6 |
| sodium chloride | 3-30 | .5-25 | 15-20 |
| ethanol | 5-30 | 7.5-20 | 9.5-15 |
| water | 15-95 | 35-90 | 65-85 |
| flavors | 0.1-5 | 1-4 | 2-3 |
| G. Calcitonin-Salmon lingual spray ||||
| calcitonin-salmon | 0.001-5 | 0.005-2 | 01-1.5 |
| ethanol | 2-15 | 3-10 | 7-9.5 |
| water | 30-95 | 50-90 | 60-80 |
| polyethylene glycol | 2-15 | 3-10 | 7-9.5 |
| sodium chloride | 2.5-20 | 5-15 | 10-12.5 |
| flavors | 0.1-5 | 1-4 | 2-3 |
| H. Insulin lispro, lingual spray ||||
| insulin | 20-60 | 4-55 | 5-50 |
| glycerin | 0.1-10 | 0.25-5 | 0.1-1.5 |
| dibasic sodium phosphate | 1-15 | 2.5-10 | 4-8 |
| m-cresol, | 1-25 | 5-25 | 7.5-12.5 |
| zinc oxide | 0.01-0.25 | .05-0.15 | 0.075-0.10 |
| m-cresol | 0.1-1 | 0.2-0.8 | 0.4-0.6 |
| phenol | trace amounts | trace amounts | trace amounts |
| ethanol | 5-20 | 7.5-15 | 9-12 |
| water | 30-90 | 40-80 | 50-75 |
| propylene glycol | 5-20 | 7.5-15 | 9-12 |
| flavors | 0.1-5 | 0.5-3 | 0.75-2 | adjust pH to 7.0-7.8 with HCl or NaOH

Example 2

CNS Active Amines and their Salts: Including but not Limited to Tricyclic Amines, GABA Analogues, Thiazides, Phenothiazine Derivatives, Serotonin Antagonists and Serotonin Reuptake Inhibitors

|  | Amounts | preferred amount | most preferred amount |
|---|---|---|---|
| A. Sumatriptan succinate lingual spray ||||
|  | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |

-continued

|  | Amounts | preferred amount | most preferred amount |
|---|---|---|---|
| water | 5-30 | 7.5-20 | 10-15 |
| flavors | 0.1-5 | 1-4 | 2-3 |
| B. Sumatriptan succinate bite capsule | | | |
| sumatriptan succinate | 0.01-5 | 0.05-3.5 | 0.075-1.75 |
| polyethylene glycol | 25-70 | 30-60 | 35-50 |
| glycerin | 25-70 | 30-60 | 35-50 |
| flavors | 0.1-10 | 1-8 | 3-6 |
| C. Clozapine lingual spray | | | |
| clozapine | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |
| D. Clozapine non-polar lingual spray with propellant | | | |
| clozapine | 0.5-30 | 1-20 | 10-15 |
| MIGLYOL ® | 20-85 | 25-70 | 30-40 |
| Butanol | 5-80 | 30-75 | 60-70 |
| flavors | 0.1-5 | 1-4 | 2-3 |
| E. Clozapine non-polar lingual spray without propellant | | | |
| clozapine | 0.5-30 | 1-20 | 10-15 |
| MIGLYOL ® | 70-99.5 | 80-99 | 85-90 |
| flavors | 0.1-5 | 1-4 | 2-3 |
| F. Cyclobenzaprine non-polar lingual spray | | | |
| cyclobenzaprine (base) | 0.5-30 | 1-20 | 10-15 |
| MIGLYOL ® | 20-85 | 25-70 | 30-40 |
| Iso-butane | 15-80 | 30-75 | 60-70 |
| flavors | 0.1-5 | 1-4 | 2-3 |
| G. Dexfenfluramine hydrochloride lingual spray | | | |
| dexfenfluramine HCl | 5-30 | 7.5-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

Example 3

Sulfonylureas

|  | Amounts | preferred amount | most preferred amount |
|---|---|---|---|
| A. Glyburide lingual spray | | | |
| glyburide | 0.25-25 | 0.5-20 | 0.75-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 2.5-30 | 5-20 | 6-15 |
| flavors | 0.1-5 | 1-4 | 2-3 |
| B. Glyburide non-polar bite capsule | | | |
| glyburide | 0.01-10 | 0.025-7.5 | 0.1-4 |
| olive oil | 30-60 | 35-55 | 30-50 |
| polyoxyethylated oleic glycerides | 30-60 | 35-55 | 30-50 |
| flavors | 0.1-5 | 1-4 | 2-3 |

Example 4

Antibiotics Anti-Fungals and Anti-Virals

|  | Amounts | preferred amount | most preferred amount |
|---|---|---|---|
| A. Zidovudine [formerly called azidothymidine (AZT) (Retrovir)] non-polar lingual spray | | | |
| zidovudine | 10-50 | 15-40 | 25-35 |
| Soya oil | 20-85 | 25-70 | 30-40 |
| Butane | 15-80 | 30-75 | 60-70 |
| flavors | 0.1-5 | 1-4 | 2-3 |
| B. Erythromycin bite capsule | | | |
| erythromycin | 25-65 | 30-50 | 35-45 |
| polyoxyethylene glycol | 5-70 | 30-60 | 45-55 |
| glycerin | 5-20 | 7.5-15 | 10-12.5 |
| flavors | 1-10 | 2-8 | 3-6 |
| C. Ciprofloxacin hydrochloride bite capsule | | | |
| ciprofloxacin hydrochloride | 25-65 | 35-55 | 40-50 |
| glycerin | 5-20 | 7.5-15 | 10-12.5 |
| polyethylene glycol | 120-75 | 30-65 | 40-60 |
| flavors | 1-10 | 2-8 | 3-6 |
| D. zidovudine [formerly called azidothymidine (AZT) (Retrovir)] lingual spray | | | |
| zidovudine | 10-50 | 15-40 | 25-35 |
| water | 30-80 | 40-75 | 45-70 |
| ethanol | 5-20 | 7.5-15 | 9.5-12.5 |
| polyethylene glycol | 5-20 | 7.5-15 | 9.5-12.5 |
| flavors | 0.1-5 | 1-4 | 2-3 |

Example 5

Anti-Emetics

|  | Amounts | preferred amount | most preferred amount |
|---|---|---|---|
| A. Ondansetron hydrochloride lingual spray | | | |
| ondansetron hydrochloride | 1-25 | 2-20 | 2.5-15 |
| citric acid monohydrate | 1-10 | 2-8 | 2.5-5 |
| sodium citrate dihydrate | 0.5-5 | 1-4 | 1.25-2.5 |
| water | 1-90 | 5-85 | 10-75 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |
| B. Dimenhydrinate bite capsule | | | |
| dimenhydrinate | 0.5-30 | 2-25 | 3-15 |
| glycerin | 5-20 | 7.5-15 | 10-12.5 |
| polyethylene glycol | 45-95 | 50-90 | 55-85 |
| flavors | 1-10 | 2-8 | 3-6 |
| C. Dimenhydrinate polar lingual spray | | | |
| dimenhydrinate | 3-50 | 4-40 | 5-35 |
| water | 5-90 | 10-80 | 15-75 |
| ethanol | 1-80 | 3-50 | 5-10 |
| polyethylene glycol | 1-80 | 3-50 | 5-15 |
| sorbitol | 0.1-5 | 0.2-40 | 0.4-1.0 |
| aspartame | 0.01-0.5 | 0.02-0.4 | 0.04-0.1 |
| flavors | 0.1-5 | 1-4 | 2-3 |

Example 6

Histamine H-2 Receptor Antagonists

|  | Amounts | preferred amount | most preferred amount |
|---|---|---|---|
| A. Cimetidine hydrochloride bite capsule | | | |
| cimetidine HCl | 10-60 | 15-55 | 25-50 |
| glycerin | 5-20 | 7.5-15 | 10-12.5 |
| polyethylene glycol | 20-90 | 25-85 | 30-75 |
| flavors | 1-10 | 2-8 | 3-6 |
| B. Famotidine lingual spray | | | |
| famotidine | 1-35 | 5-30 | 7-20 |
| water | 2.5-25 | 3-20 | 5-10 |
| L-aspartic acid | 0.1-20 | 1-15 | 5-10 |
| polyethylene glycol | 20-97 | 30-95 | 50-85 |
| flavors | 0.1-10 | 1-7.5 | 2-5 |
| C. Famotidine non-polar lingual spray | | | |
| famotidine | 1-35 | 5-30 | 7-20 |
| Soya oil | 10-50 | 15-40 | 15-20 |
| Butanol | 5-80 | 30-75 | 45-70 |
| polyoxyethylated oleic glycerides | 10-50 | 15-40 | 15-20 |
| flavors | 0.1-5 | 1-4 | 2-3 |

Example 7

Barbiturates

|  | Amounts | preferred amount | most preferred amount |
|---|---|---|---|
| A. Phenytoin sodium lingual spray | | | |
| phenytoin sodium | 10-60 | 15-55 | 20-40 |
| water | 2.5-25 | 3-20 | 5-10 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |
| B Phenytoin non-polar linqual spray | | | |
| phenytoin | 5-45 | 10-40 | 15-35 |
| MIGLYOL ® | 10-50 | 15-40 | 15-20 |
| Butane | 15-80 | 30-75 | 60-70 |
| polyoxyethylated oleic glycerides | 10-50 | 15-40 | 15-20 |
| flavors | 0.1-10 | 1-8 | 5-7.5 |

Example 8

Prostaglandins

|  | Amounts | preferred amount | most preferred amount |
|---|---|---|---|
| A. Carboprost tromethamine lingual spray | | | |
| carboprost tromethamine | 0.05-5 | 0.1-3 | 0.25-2.5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| sodium chloride | 1-20 | 3-15 | 4-8 |
| flavors | 0.1-5 | 1-4 | 2-3 |
| B. Carboprost non-polar lingual spray | | | |
| carboprost | 0.05-5 | 0.1-3 | 0.25-2.5 |
| MIGLYOL ® | 25-50 | 30-45 | 35-40 |
| Butane | 5-60 | 10-50 | 20-35 |
| polyoxyethylated oleic glycerides | 25-50 | 30-45 | 35-40 |
| flavors | 0.1-10 | 1-8 | 5-7.5 | pH is adjusted with sodium hydroxide and/or hydrochloric acid

Example 9

Neutraceuticals

|  | Amounts | amount preferred | most preferred amount |
|---|---|---|---|
| A. Carnitine as bite capsule (contents are a paste) | | | |
| carnitine fumarate | 6-80 | 30-70 | 45-65 |
| soya oil | 7.5-50 | 10-40 | 12.5-35 |
| soya lecithin | 0.001-1.0 | 0.005-0.5. | 01-0.1 |
| Soya fats | 7.5-50 | 10-40 | 12.5-35 |
| flavors | 1-10 | 2-8 | 3-6 |
| B. Valerian as lingual spray | | | |
| valerian extract | 0.1-10 | 0.2-7 | 0.25-5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| flavors | 1-10 | 2-8 | 3-6 |
| C. *Echinacea* as bite capsule | | | |
| *echinacea* extract | 30-85 | 40-75 | 45-55 |
| soya oil | 7.5-50 | 10-40 | 12.5-35 |
| soya lecithin | 0.001-1.0 | 0.005-0.5 | 01-0.1 |
| Soya fats | 7.5-50 | 10-40 | 12.5-35 |
| flavors | 1-10 | 2-8 | 3-6 |
| D. Mixtures of ingredients | | | |
| magnesium oxide | 15-40 | 20-35 | 25-30 |
| chromium picolinate | 0.01-1.0 | 0.02-0.5 | .025-0.75 |
| folic acid | .025-3.0 | 0.05-2.0 | 0.25-0.5 |
| vitamin B-12 | 0.01-1.0 | 0.02-0.5 | .025-0.75 |
| vitamin E | 15-40 | 20-35 | 25-30 |
| Soya oil | 10-40 | 12.5-35 | 15-20 |
| soya lecithin | 0.1-5 | 0.2-4 | 0.5-1.5 |
| soya fat | 10-40 | 15-35 | 17.5-20 |

Example 10

Sleep Inducers (Also CNS Active Amine)

A. Diphenhydramine hydrochloride lingual spray

|  | Amounts | preferred amount | most preferred amount |
|---|---|---|---|
| diphenhydramine HCl | 3-50. | 4-40 | 5-35 |
| water | 0 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 11

Anti-Asthmatics-Bronchodilators

|  | Amounts | preferred amount | most preferred amount |
|---|---|---|---|
| A. Isoproterenol Hydrochloride as polar lingual spray | | | |
| isoproterenol Hydrochloride | 0.1-10 | .2-7.5 | 0.5-6 |
| water | 5-90 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |
| B. Terbutaline sulfate as polar linqual spray | | | |
| terbutaline sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |
| C. Terbutaline as non-polar lingual spray | | | |
| terbutaline | 0.1-10 | 0.2-7.5 | 0.5-6 |
| MIGLYOL ® | 25-50 | 30-45 | 35-40 |
| isobutane | 5-60 | 10-50 | 20-35 |
| polyoxyethylated oleic glycerides | 25-50 | 30-45 | 35-40 |
| flavors | 0.1-10 | 1-8 | 5-7.5 |
| D. Theophylline polar bite capsule | | | |
| theophylline | 5-50 | 10-40 | 15-30 |
| polyethylene glycol | 20-60 | 25-50 | 30-40 |
| glycerin | 25-50 | 35-45 | 30-40 |
| propylene glycol | 25-50 | 35-45 | 30-40 |
| flavors | 0.1-5 | 1-4 | 2-3 |
| E. Albuterol sulfate as polar lingual spray | | | |
| albuterol sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 12

Polar Solvent Formulations Using a Propellant

|  | Amount | Preferred Amount | Most-Preferred Amount |
|---|---|---|---|
| A. Sulfonylurea | | | |
| glyburide | 0.1-25% | 0.5-15% | 0.6-10% |
| Ethanol | 40-99% | 60-97% | 70-97% |
| Water | 0.01-5% | 0.1-4% | 0.2-2% |
| Flavors | 0.05-10% | 0.1-5% | 0.1-2.5% |
| Propellant | 2-10% | 3-5% | 3-4% |
| B. Prostaglandin E (vasodilator) | | | |
| prostaglandin $E_1$ | 0.01-10% | 0.1-5% | 0.2-3% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |
| C. Promethazine (antiemetic, sleep inducer, and CNS active amine) | | | |
| promethazine | 1-25% | 3-15% | 5-12% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |
| D. Meclizine | | | |
| meclizine | 1-25% | 3-15% | 5-12% |
| Ethanol | 1-15% | 2-10% | 3-6% |
| Propylene glycol | 20-98% | 5-90% | 10-85% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

Example 13

Zolpidem Formulations

| Component | Percent (w/w) |
|---|---|
| A. A propellant free zolpidem formulation containing a polar solvent has the following formula: | |
| Zolpidem tartrate | 2.5 |
| Propylene glycol | 15 |
| Glycerol | 10 |
| Bitter mask | 0.2 |
| Benzalkonium chloride | 0.1 |
| Citrate buffer (1N, pH 6) | 8 |
| Ethanol | QS 100 mL |
| B. A zolpidem formulation in a polar solvent with a propellant has the following formula: | |
| Zolpidem tartrate | 2.5 |
| Ethanol | 35 |
| Glycerol | 10 |
| Bitter mask | 0.2 |
| Butane | QS 100 |
| C. A propellant free zolpidem formulation in a mixture of a polar and a non-polar solvent has the following formula: | |
| Zolpidem tartrate | 0.5 |
| MIGLYOL ® | 15 |
| Lemon oil | 10 |
| Ethanol | QS to 100 mL |

-continued

| Component | Percent (w/w) |
|---|---|
| D. A zolpidem formulation in a mixture of a polar solvent and a non-polar solvent with a propellant can be made according to the following formula: | |
| Zolpidem tartrate | 0.5 |
| Liquid paraffin | 15 |
| Lemon oil | 10 |
| Ethanol | 40 |
| Butane | QS 100 |
| E. A propellant free zolpidem formulation in a non-polar solvent can be made according to the following formula: | |
| Zolpidem Tartrate | 0.2 |
| Lemon oil | 0.1 |
| MIGLYOL ® | Qs to 100 |
| F. A zolpidem formulation in a non-polar solvent with a propellant can be made according to the following formula: | |
| Zolpidem Tartrate | 0.2 |
| Lemon oil | 0.1 |
| MIGLYOL ® | 50 |
| Butane | Qs to 100 |

What is claimed is:

1. A method of administering zolpidem to a mammal to provide transmucosal absorption of a pharmacologically effective amount of zolpidem through the oral mucosa of the mammal to the systemic circulatory system of the mammal, comprising:

spraying the oral mucosa of the mammal with a buccal spray composition comprising in weight percent of the composition: zolpidem or a pharmaceutically acceptable salt thereof in an amount of between 0.1 and 25 percent by weight of the total composition; a polar solvent in an amount between 10 and 97 percent by weight of the total composition; and a propellant in an amount between 2 and 10 percent by weight of the total composition, wherein said propellant is a $C_3$ to $C_8$ hydrocarbon of linear or branched configuration; and wherein said spraying the oral mucosa results in transmucosal absorption of a pharmacologically effective amount of zolpidem through the oral mucosa to the systemic circulatory system of said mammal.

2. The method of claim 1, wherein the composition further comprises a taste mask and/or flavoring agent in an amount between 0.05 and 10 percent by weight of the total composition.

3. The method of claim 2, wherein the polar solvent is present in an amount between 20 and 97 percent by weight of the total composition, the zolpidem or a pharmaceutically acceptable salt thereof is present in an amount between 0.1 and 15 percent by weight of the total composition, the propellant is present in an amount between 2 and 5 percent by weight of the composition, and the taste mask and/or flavoring agent is present in an amount between 0.1 and 5 percent by weight of the total composition.

4. The method of claim 3, wherein the polar solvent is present in an amount between 25 and 97 percent by weight of the total composition, the zolpidem or a pharmaceutically acceptable salt thereof is present in an amount between 0.2 and 10 percent by weight of the total composition, the propellant is present in an amount between 2 and 4 percent by weight of the composition, and taste mask and/or flavoring agent is present in an amount between 0.1 and 2.5 percent by weight of the total composition.

5. The method of claim 1, wherein the polar solvent is selected from the group consisting of polyethyleneglycols having a molecular weight between 400 and 1000, $C_2$ to $C_8$ mono- and poly-alcohols, and $C_7$ to $C_{18}$ alcohols of linear or branched configuration.

6. The method of claim 1, wherein the polar solvent comprises polyethylene glycol.

7. The method of claim 1, wherein the polar solvent comprises ethanol.

8. The method of claim 2, wherein the flavoring agent is selected from the group consisting of synthetic or natural oil of peppermint, oil of spearmint, citrus oil, fruit flavors, sweeteners, and mixtures thereof.

9. The method of claim 1, wherein the propellant is selected from the group consisting of propane, N-butane, iso-butane, N-pentane, iso-pentane, neo-pentane, and mixtures thereof.

10. The method of claim 1, wherein the amount of the spray is predetermined.

* * * * *